United States Patent [19]

Tanaka

[11] 4,299,567
[45] Nov. 10, 1981

[54] SUPPORT STRUCTURE

[76] Inventor: Asami Tanaka, 9307 N. Lavergne, Skokie, Ill. 60077

[21] Appl. No.: 117,543

[22] Filed: Feb. 1, 1980

[51] Int. Cl.³ .............................................. F27D 5/00
[52] U.S. Cl. .................................. 432/253; 432/258; 432/259
[58] Field of Search ...................... 432/253, 258, 259

[56] References Cited

U.S. PATENT DOCUMENTS

| | | | |
|---|---|---|---|
| 3,819,322 | 6/1974 | Bocian et al. | 432/259 |
| 3,861,867 | 1/1975 | Ouhl | 432/259 |
| 4,136,449 | 1/1979 | Penrod et al. | 432/258 |
| 4,184,840 | 1/1980 | Gamberg et al. | 432/259 |

Primary Examiner—John J. Camby

Attorney, Agent, or Firm—Neuman, Williams, Anderson & Olson

[57] ABSTRACT

An improved kiln or oven useable support structure is provided which includes a base having a surface with a plurality of vertically oriented support bores disposed thereacross. A plurality of straight and crank shaped support pins having predetermined cross-sections are removably insertable into the bores of said base. A curved support member has in one end an aperture having a configuration minimally larger than the cross-section of said support pins. When said aperture encircles a support pin and the axis of said aperture is substantially parallel with said pin the two move freely with respect to one another, but when the axis of said aperture is not substantially parallel with said pin, the two pinch-lock or bind to maintain their relative positions.

19 Claims, 3 Drawing Figures

U.S. Patent    Nov. 10, 1981    4,299,567
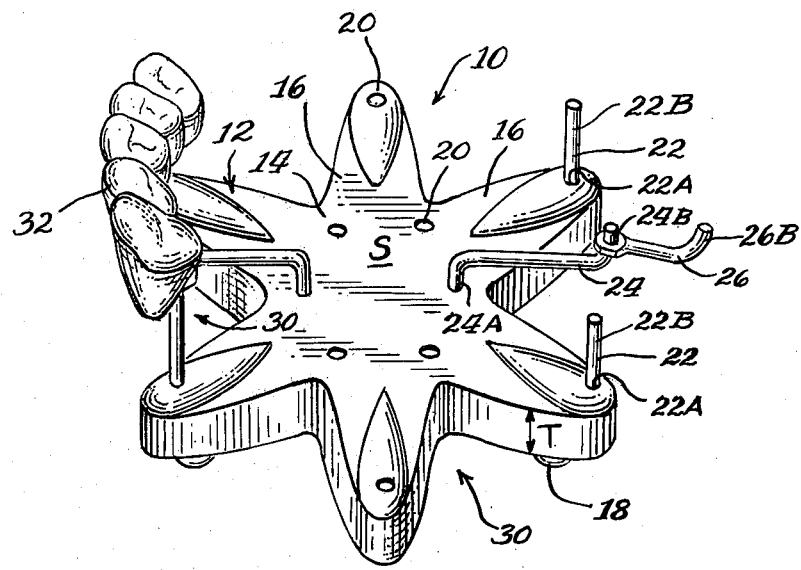
Fig. 1.
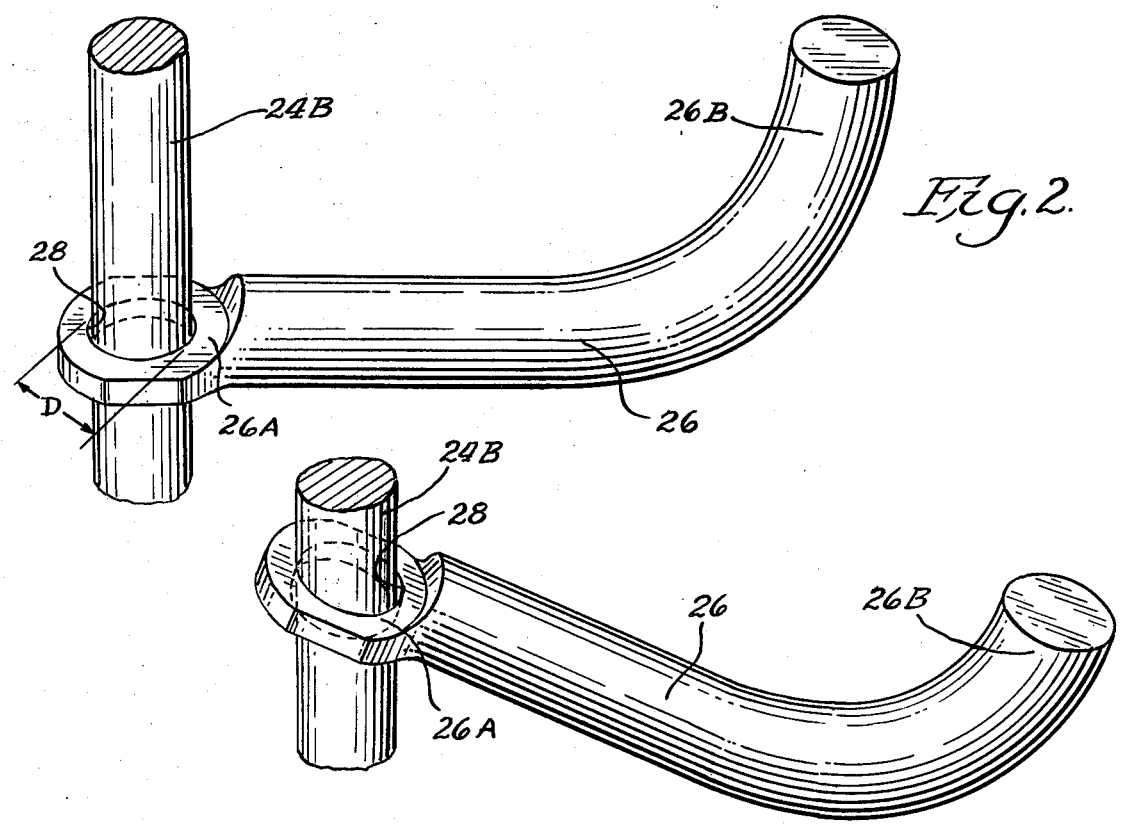
Fig. 2.
Fig. 3.

SUPPORT STRUCTURE

BACKGROUND OF THE INVENTION

In the fabrication of prosthetic dental devices or dental restoratives it is necessary to bake or kiln-fire the restorative itself or portions thereof, as well as materials used in intermediate steps resulting in the final device. When baking the restorative it is essential to support it above the oven or kiln floor to avoid contamination and physical damage and to promote uniform heat distribution. Further, the restorative must be supported from the underside to avoid any damage to the outer surface. This task is complicated by the fact that each prosthetic device, such as a dental bridge or crown, is custom designed and personally fitted, thereby having a unique shape and size. Accordingly, each restorative requires a uniquely shaped or configured support device.

In an effort to accomplish these ends porcelain firing trays were developed that included a base with integrally cast upwardly extending supports, such as cones. However, fixed supports such as these fail to provide the versatility to adequately support prosthetic devices of varying shapes and sizes because the cones are not moveable with respect to one another and they are all of a fixed uniform height. Other procelain supports include a pegboard design having uniformly spaced peg holes and moveable support pegs. These pegboard trays offer some versatility, but, even with a variety of peg configurations, are still restricted to a limited number of support combinations as determined by the location of the uniformly spaced peg holes and the fixed length of the pegs.

A still further drawback is the rectangular or circular configuration of the support base, which, in the prior art devices, is disposed below the entire prosthetic device while it is baked in order to lend sufficient support to the vertical pins or pegs. The proximity of the base and prosthetic device impedes the convection heat flow around the device resulting in non-uniform and inconsistent baking.

SUMMARY OF THE INVENTION

Accordingly, it is an object of the present invention to provide an improved support structure suitable for use in a kiln or oven which readily avoids the aforenoted problems.

It is a further object to provide an effective support for dental prosthetic devices of varying shapes and sizes, said support being conveniently adjustable without the need for special tools.

It is a still further object to provide an improved support for dental prosthetic devices whereby the supporting members may be positioned in a wide variety of vertical and horizontal combinations.

It is a still further object to provide a support for dental prosthetic devices that promotes a uniform heat flow around the supported device.

Further and additional objects will become apparent from the description, accompanying drawings, and appended claims.

In accordance with an embodiment of the invention, a heat resisting support structure is provided which includes a base portion having an upper surface with a plurality of support bores disposed thereacross and extending downwardly into said base. A plurality of support pins, each having a predetermined cross-section, is provided for removable insertion into said support bores. At least one curved support member is provided having an aperture disposed proximate one end thereof, said aperture having a configuration minimally larger than the cross-section of a support pin and its axis generally perpendicular to the longitudinal axis of said end of said curved member. When said aperture encircles a support pin and the axis of said aperture is substantially parallel with said pin the two move freely with respect to each other, but when the axis of said aperture is not substantially parallel with said pin, the two pinch-lock or bind to maintain their relative positions.

BRIEF DESCRIPTION OF THE DRAWINGS

FIG. 1 is an elevated perspective view of one configuration of the improved support device, including both straight and crank-shaped support pins.

FIG. 2 is an elevated perspective view of the curved support member of FIG. 1 with its aperture encircling a support pin and the axis of said aperture substantially parallel with said pin.

FIG. 3 is an elevated perspective view of the curved support member of FIG. 1 with its aperture encircling a support pin and the axis of said aperture not substantially parallel with said pin, resulting in a pinch-lock.

DESCRIPTION OF THE ILLUSTRATED EMBODIMENT

Referring now to FIG. 1, an improved heat resisting support structure 10, suitable for use in a kiln or oven, is provided and includes a base 12 having a central portion 14 and a plurality of connected radially outwardly extending arm portions 16. The base 12 is typically made of a heat resistant or refractory material, such as a ceramic, and has an upper surface S and a predetermined thickness T. The radial arm portions 16 may have any desired length or cross-sectional shape, and are connected to and typically integrally cast with the base portion 14 to form a unitary structure. The number of arm portions 16 may vary as necessary or desireable. The dimensions of both the base and arm portions may be chosen to suit the user's needs and to provide sufficient structural integrity to withstand repeated use and reasonably expected abuse.

A plurality of support pads or feet 18 support the base above the kiln or oven floor upon which they rest. A plurality of support bores 20 of a predetermined diameter or other cross-sectional shape are disposed across the upper surface S of the base 12 and extend generally vertically downwardly into the base. Each of the bores 20 preferably has a depth less than the base thickness T, but sufficiently deep to maintain a pin or other support in a generally vertical position. These bores may be drilled or formed in any convenient manner and may be located as necessary or desireable.

A plurality of rigid straight support pins 22 are provided, each having a first end 22A and a second end 22B. The first end 22A and the bores 20 have complemental configurations so as to provide a sliding fit between the pin end 22A and a corresponding bore. The second end 22B has a predetermined cross-sectional configuration, and makes contact with the dental restorative being heated and supports same above the base 12. The second end 22B may have the same cross-section as the first end 22A. Crank-shaped or non-rectiliniar support pins 24 may be substituted for or used in conjunction with the straight pins 22. The first and second ends 24A and 24B of pins 24 may be shaped in the same way as pins 22. However, inherent with the shape of the crank pin 24 is the ability to position the second end 24B in a variety of radial positions with respect to the pin-supporting bore 20.

Referring also to FIG. 2, there is provided a curved support member or extension 26 having a first end 26A and a second end 26B. Proximate said first end 26A is an aperture 28 with its axis generally perpendicular to the longitudinal axis of said first end 26A of said curved member 26. Said aperture 28 is preferably formed as a part of the member 26 itself and has a diameter or other cross-sectional configuration minimally larger than that of the second end of the support pins 22 and 24. This permits the aperture 28 to encircle one of said pins 22 or 24 and slide freely with respect thereto when the axis of said aperture is substantially parallel to the longitudinal axis of the pin, so that said curved member 26 may be positioned both radially and axially with respect to said pin 22 or 24.

Referring now to FIG. 3, once said curved member 26 has been selectively positioned radially and axially with respect to a support pin 22, 24, the axis of the aperture is tilted or skewed relative to the axis of the pin and results in a pinch-lock or bind occurring between member 26 and pin 22, 24. Once there is a pinch-lock or binding condition, the second end 26B of member 26 will remain substantially stationary and supportingly engage the underside of a dental restorative.

The member 26 may be used in any combination with the pins 22, 24 so as to provide the necessary support for dental restoratives which may vary in size and shape over a wide range. Said members and pins may assume any convenient or desired configuration or shape. This permits the user to conveniently and quickly provide an unlimited array of supports without being limited to a predetermined pattern or height, as characterized by the prior art.

Referring again to FIG. 1, the generally star-shaped configuration of the base 12, formed by the radial arm portions 16, defines a plurality of heat flow zones 30 between adjacent arms. These zones enhance the convection heat flow around the supported dental restorative 32 by expanding the volume between the dental restorative and the base 12. The heat flow is further enhanced by the space provided between the underside of the base 12 and the floor of the oven; said space being created by the pads or feet 18 attached to the underside of the base. Such an improved heat flow results in more uniform and consistent baking.

While the invention has heretofore been described in detail with particular reference to illustrated embodiments, it is to be understood, of course, that variations, modifications, and the substitution of equivalent mechanisms can be effected without departing from the scope of this invention.

What is claimed is:

1. A heat resisting structure for supporting an article above a surface while the article is being subjected to a predetermined amount of heat, said structure comprising a base section; a first support means selectively attached to said base and extending generally upwardly therefrom; and a second support means in adjustable complimental engagement with said first support means, said second support means having one portion thereof adapted to supportingly engage the article and a second portion thereof including selective locking means cooperating with said first support means, the relative position of said second support with respect to said first support means being selectively adjustable.

2. A structure as in claim 1 wherein said base section and said first support means are selectively separable.

3. A structure as in claim 1 wherein said base comprises at least one support bore extending generally vertically downwardly into said base portion.

4. A structure as in claim 3 wherein said first support means is selectively disposed in said bores.

5. A structure as in claim 1 wherein said first support means comprises a first end and a second end.

6. A structure as in claim 1 wherein said first support means comprises members of varying configurations.

7. A structure as in claim 5 wherein said first support means comprises a first end disposed generally collinear said second end.

8. A structure as in claim 5 wherein said first support means comprises a first end disposed generally parallel said second end.

9. A structure as in claim 1 wherein said second support means comprises a curved support member.

10. A structure as in claim 1 wherein said second support means comprises a first end and a second end.

11. A structure as in claim 1 wherein said second support means comprises members of varying configurations.

12. A structure as in claim 10 wherein said second support means comprises a first end with its longitudinal axis disposed generally perpendicular the longitudinal axis of said second end.

13. A second support means as in claim 10 comprising a first end having an aperture with its axis generally perpendicular to the longitudinal axis of said first end of said second support.

14. A structure as in claim 1 wherein said base portion comprises a central section and a plurality of radially outwardly extending arm portions connected to said central section, said arm portions defining a heat flow zone therebetween to enhance more uniform heat distribution around said supported item.

15. A support structure as in claim 11 wherein said base portion includes six radial arm portions.

16. A structure as in claim 1 wherein said first support means has a predetermined cross-sectional configuration.

17. A structure as in claim 16 wherein said selective locking means includes an aperture defined by said second support means second portion, said aperture complimentary to and minimally larger than the cross-sectional configuration of said first support means, whereby said second support means selectively slides or locks with respect to said first support means.

18. A structure as in claim 1 wherein said second support means is in complimental engagement solely with said first support means independent of said base.

19. A structure as in claim 1 wherein said second support means is selectively adjustable both radially and axially with respect to said first support means.

* * * * *